United States Patent [19]

Yokozeki et al.

[11] Patent Number: 4,970,148
[45] Date of Patent: Nov. 13, 1990

[54] METHOD OF PRODUCING 2′,3′-DIDEOXYINOSINE

[75] Inventors: Kenzo Yokozeki; Hideyuki Shirae; Katsunori Kobayashi; Hiroshi Shiragami; Yasuo Irie, all of Kawasaki, Japan

[73] Assignee: Ajinomoto Co., Inc., Tokyo, Japan

[21] Appl. No.: 254,584

[22] Filed: Oct. 7, 1988

[30] Foreign Application Priority Data

Oct. 7, 1987 [JP] Japan .............................. 62-253382
Dec. 24, 1987 [JP] Japan .............................. 62-327790
Sep. 13, 1988 [JP] Japan .............................. 63-229585

[51] Int. Cl.$^5$ .................. C12P 19/40; C12P 19/38; C12P 19/30; C12P 1/04
[52] U.S. Cl. ................................. 435/88; 435/87; 435/89; 435/170; 435/822
[58] Field of Search ................. 435/88, 89, 92, 170, 435/87, 822

[56] References Cited

U.S. PATENT DOCUMENTS

| | | | |
|---|---|---|---|
| 3,111,459 | 11/1963 | Motozaki et al. | 435/88 |
| 3,488,257 | 1/1970 | Suzuki et al. | 435/88 |
| 3,616,207 | 10/1971 | Yoneda et al. | 435/88 |
| 3,616,212 | 10/1971 | Abe et al. | 435/88 |
| 3,625,825 | 1/1969 | Shibai et al. | 435/88 |
| 3,634,193 | 1/1972 | Nakao et al. | 435/88 |
| 3,960,661 | 6/1976 | Enei et al. | 435/88 |
| 4,578,336 | 3/1986 | Sumino et al. | 435/88 |

FOREIGN PATENT DOCUMENTS

| | | | |
|---|---|---|---|
| 0080864 | 6/1983 | European Pat. Off. | 435/88 |
| 0040758 | 12/1971 | Japan | 435/88 |
| 0038198 | 9/1972 | Japan | 435/88 |
| 0175895 | 10/1984 | Japan | 435/92 |
| 2014794 | 1/1987 | Japan | 435/88 |

OTHER PUBLICATIONS

Lehninger, A. L., Biochemistry (2nd ed.), Worth Publishers, Inc., 1975, pp. 741–742; 218, 244.
Gherna et al., eds., American Type Culture Collection Catalogue of Bacteria, Phabes and rDNA Vectors, 16th ed., 1985, pp. 5, 10, 14, 21, 39, 43, 45, 63, 80, 85, 87, 99–101, 114, 123, 128, 130, 142, 150, 158, 159, 167, 213.
Inst. for Fern., Osaka, List of Cultures, 8th ed., vol. 1, 1988, p. 105.
J. L. York and G. A. LePage, "A Kinetic Study of the Deamination of Some Adenosine . . . ", Can. J. Biochem., 44, 331–7 (1966).
S. Frederiksen, "Specificity of Adenosine Deaminase Toward . . . ", Arch. Bioche. & Biophs., 113, 383–388 (1966).
R. Wolfenden et al., "Substrate Binding by Adenosine Deaminase", J. Biol. Chem., 242, 977–983 (1967).
Alexander Bloch et al., "The Role of the 5′-Hydroxyl Group of Adenosine . . . ", J. Med. Chem., 10, 908–912 (1967).
L. Toji & S. S. Cohen, "Termination of Deoxyribonucleic Acid . . . ", J. Bacteriol, 103, 323–328 (1970).
S. P. Colowick & N. O. Kaplan, editors, Methods in Enzymology, vol. II, Academic Press Inc., N.Y. ., p. 473–477 (1955).
S. Akabori, editor, Enzyme Handbook, Asakura Shoten, Ltd., Japan, pp. 559–5960 (1966) (English translation also included).

Primary Examiner—Barry S. Richman
Assistant Examiner—Stephanie W. Zitomer
Attorney, Agent, or Firm—Oblon, Spivak, McClelland, Maier & Neustadt

[57] ABSTRACT

A method of producing dideoxyinosine involving contacting as a substrate 2′,3′-dideoxyadenosine with a microorganism which is capable of converting the substrate into 2′,3′-dideoxyinosine.

6 Claims, No Drawings

METHOD OF PRODUCING 2',3'-DIDEOXYINOSINE

BACKGROUND OF THE INVENTION

1. Field of the Invention

The present invention relates to a method of producing 2',3'-dideoxyinosine from 2',3'-dideoxyadenosine.

2. Description of the Related Art

2',3'-Dideoxyinosine has a potent anti-viral activity and is thus expected to be a therapeutic agent for viral diseases such as influenza, AIDS, etc.

As a method for synthesis of dideoxynucleosides such as 2'3'-dideoxyinosine, etc. which are conventionally known, deoxygenation of nucleosides at the 2'- or 3'-position is known as is reported in Chem. Pharm. Bull., 22, 128 (1974). However, only a few such cases are reported because a protective group must be introduced prior to the reaction, the reaction occurs at the 2'- or 3'-position with difficulty due to serious steric hindrance, and vigorous reaction conditions or reactants cannot be used due to unstability of nucleosides under severe conditions. Thus, no industrially satisfactory method has been established.

Against this background, the present inventors previously developed a method of producing 2',3'-dideoxynucleosides such as 2',3'-dideoxyinosine, 2',3'-dideoxyadenosine, etc. from 2',3'-dideoxyuridine or 2,3-dideoxyribose-1-phosphate by the action of microorganisms (Japanese Patent Application No. 62-149893).

However, this method is effective but there remains a defect in that the yield is somewhat poor in the case of producing 2',3'-dideoxyinosine.

Furthermore, an attempt to convert 2',3'-dideoxyadenosine into 2',3'-dideoxyinosine using animal organ-derived adenosine deaminase was made (Biochim. Biophys. Acta, 566 (2), 259 (1979)) but since the enzyme is derived from an animal source, the method is not suited from the viewpoints of both cost and supply.

Conventional chemical methods for synthesizing 2',3'-dideoxyinosine are all defective in that many reaction steps are involved and the yield is poor.

SUMMARY OF THE INVENTION

Accordingly, the problem to be solved by the present invention is to provide a method of efficiently producing 2',3'-dideoxyinosine in a high yield.

As has been previously shown, a method of converting 2',3'-dideoxyadenosine into 2',3'-dideoxyinosine is already known in the case of using animal organ-derived adenosine deaminase but quite unknown with respect to microorganism-derived enzymes. In general, an animal-derived enzyme has substrate specificity over a wide range (in the case described above, adenosine deaminase capable of converting adenosine into inosine acts on 2',3'-dideoxyadenosine to produce 2',3'-dideoxyinosine). On the other hand, it is known that in general microorganism-derived enzymes have a relatively narrow substrate specificity.

An object of the present invention is to establish a method for converting 2',3'-dideoxyadenosine into 2',3'-dideoxyinosine at low cost, either by discovering a microorganism capable of producing an enzyme having substrate specificity over a wide range as in the animal-derived enzyme, pursuing an enzyme solution capable of converting 2',3'-dideoxyadenosine into 2',3'-dideoxyinosine from an industrially suitable microorganism or by discovering microorganisms capable of producing at least one enzyme specifically acting on 2',3'-dideoxyadenosine.

As a result of extensive investigations to achieve such objects, the present invention has revealed for the first time that 2',3'-dideoxyinosine can be produced from 2',3'-dideoxyadenosine (which in turn can be supplied from 2',3'-dideoxyuridine or 2,3-dideoxyribose-1-phosphate previously developed in a high yield) by the action of certain microorganisms stably at low cost, by contacting, e.g. cells of said microorganisms on the substrate.

DETAILED DESCRIPTION OF THE PREFERRED EMBODIMENTS

The present invention relates to a method of producing dideoxyinosine which comprises contacting 2',3'-dideoxyadenosine with a culture solution of a microorganism capable of converting 2',3'-dideoxyadenosine to 2',3'-dideoxyinosine and belonging to the genus Achromobacter, Acinetobacter, Aeromonas, Agrobacterium, Alcaligenes, Arthrobacter, Bacillus, Brevibacterium, Cellulomonas, Citrobacter, Corynebacterium, Escherichia, Enterobacter, Erwinia, Flavobacterium, Hafnia, Klebsiella, Kluyvera, Microbacterium, Micrococcus, Mycoplana, Nocardia, Planococcus, Protaminobacter, Proteus, Pseudomonas, Rhizobium, Rhodococcus, Salmonella, Sarcina, Serratia, Staphylococcus, Streptomyces, Vibrio or Xanthomonas, a cell thereof or a cell-derived product and producing and accumulating 2',3'-dideoxyinosine.

2',3'-Dideoxyinosine can be obtained, of course, by the method described above (directly producing 2',3'-dideoxyinosine from 2',3'-dideoxyuridine or 2,3-dideoxyribose-1-phosphate). However, with respect to production of 2',3'-dideoxyinosine, the present invention provides a much higher reaction yield and is therefore more advantageous than the previously developed method. Examples of microorganisms that can be used in the present invention include the following:

*Achromobacter candidans* FERM-P 8778
*Acinetobacter lwoffii* ATCC-9036
*Aeromonas salmonicida* ATCC-14174
*Agrobacterium tumefaciens* FERM-P 2343
*Alcaligenes faecalis* FERM BP-940
*Arthrobacter citreus* ATCC-11624
*Bacillus firmus* ATCC-8247
*Brevibacterium pusillum* ATCC-19096
*Cellulomonas flavigena* ATCC-491
*Citrobacter freundii* ATCC-8090
*Corynebacterium aquaticum* ATCC-14665
*Escherichia coli* FERM-P 7404
*Enterobacter cloacae* ATCC-13047
*Erwinia carotovora* FERM-P 2766
*Flavobacterium aquatile* ATCC-8375
*Hafnia alvei* ATCC-9760
*Klebsiella pneumoniae* ATCC-8308
*Kluyvera citrophila* FERM-P 8193
*Microbacterium imperiable* ATCC-8365
*Micrococcus luteus* ATCC-400
*Mycoplana dimorpha* ATCC-4279
*Nocardia restricta* ATCC-14887
*Planococcus citreus* ATCC-15234
*Protaminobacter alboflavus* ATCC-8458
*Proteus rettgeri* FERM BP-941
*Pseudomonas oleovorans* ATCC-8062
*Rhizobium meliloti* FERM-P 8197
*Rhodococcus rhodochrous* ATCC-12974

*Salmonella typhimurium* FERM-P 9470
*Sarcina albida* FERM BP-2472 also known as *Arthrobacter ureafaciens* FERM BP-2472
*Serratia grimesii* ATCC-14460
*Staphylococcus epidermidis* ATCC-155
*Streptomyces flavovirens* IFO-3197
*Vibrio metschnikovii* ATCC-7708
*Xanthomonas citri* FERM-P 3396.

In the above list the abbreviation "ATCC" stands for American Type Culture Collection which is located at 12301 Parklawn Drive, Rockville, Md. 20852. The abbreviation "FERM" stands for Fermentation Research Institute Agency of Industrial Science and Technology, 1-3, Higashi, 1 chome, Yatabe-machi Tsukuba-gun Ibaraki-ken, 305, Japan. The abbreviation "IFO" stands for Institute for Fermentation, Osaka 17-85, Juso-honmachi 2-chome, Yodogawa-ku, Osaka 532, Japan.

The microorganism used in the present invention is not particularly limited to those described above as long as it is capable of producing 2',3'-dideoxyinosine by deamination of 2',3'-dideoxyadenosine.

To convert 2',3'-dideoxyadenosine into 2',3'-dideoxyinosine by culturing the microorganism, the microorganism of the present invention may be cultured in a medium containing 2',3'-dideoxyadenosine from the beginning of culture or 2',3'-dideoxyadenosine may be supplemented in the medium during the course of culture.

The medium used for culturing the microorganism is an ordinary medium containing carbon sources, nitrogen sources, inorganic ions and if necessary, further contains organic nutrient sources, in addition to 2',3'-dideoxyadenosine.

As the carbon source, carbohydrates such as glucose, etc., alcohols such as glycerol, etc., organic acids and the like may be appropriately used. As the nitrogen source, ammonia gas, ammonia water, ammonium salts and the like can be used. As the inorganic ions, magnesium ions, phosphate ions, potassium ions, iron ions, manganese ions and the like may be appropriately used depending upon necessity. As the organic nutrient source, vitamins, amino acids, etc. and yeast extract, peptone, meat extract, corn steep liquor, casein hydrolyzates and others containing them may be appropriately used.

Culture is performed under aerobic conditions while controlling the pH to 5 to 8 at temperatures in an appropriate range of 25° to 40° C. to give desired results.

Thus, incubation for 1 day to 10 days results in efficient conversion of 2',3'-dideoxyadenosine into 2',3'-dideoxyinosine.

On the other hand, in the case of contacting a culture solution of the microorganism or its cell-treated products with 2',3'-dideoxyadenosine in an aqueous solution to allow them to react, microorganism cells containing the enzyme and a culture solution, etc. containing the same can be used; in addition, treated products thereof can also be used.

As the treated products, products obtained by drying the cells with acetone, homogenates of the cells, products obtained by treating the cells with ultrasonic waves, products obtained by treating the cells with a surface active agent, toluene, etc., products obtained by treating the cells with an enzyme such as lysozyme, etc., a protein fraction obtained by extracting protein from the cells and separating the proteins by means of salting out, column chromatography, etc., purified products of the protein fraction having an enzyme activity required for the desired reaction, and immobilized cells and treated products thereof, etc. are all utilizable. In general, it can be determined if a material derived from any one of the cells disclosed herein is capable of carrying out the desired transformation by contacting the cell treated product with the substrate, i.e. 2',3'-dideoxyadenosine, under the conditions reported herein in the Examples section, and determining whether 2',3'-dideoxyinosine is produced in significant quantities. Once one of ordinary skill in the art appreciates that certain microorganisms can carry out the desired transformation disclosed herein, this person will be able to derive fractions obtained from the whole cells, which fractions are capable of carrying out the same transformation. These fractions can be produced by standard methods known to those of ordinary skill in the art, in conjunction with an assay for 2',3'-dideoxyinosine. Thus, in general, any fraction derived from the whole cells reported herein which also contains an activity for producing a significant quantity of 2',3'-dideoxyinosine from 2',3'-dideoxyadenosine is also covered by the present invention.

It is appropriate that a concentration of 2',3'-dideoxyadenosine used as substrate be approximately 1 to 5000 mM, preferably 10 to 500 mM. 2',3'-Dideoxyadenosine may be added in whole amounts at the outset of the reaction or portion-wise during the course of the reaction. The culture solution of microorganism, cells or cell treated products are added to an aqueous solution containing the substrate. After adjusting a pH value in a range of 3 to 10, preferably 4 to 9, the mixture is settled or maintained at 5° to 70° C., preferably 20° to 60° C. for 10 minutes to 10 days, while agitating, whereby the reaction proceeds and the desired 2',3'-dideoxyinosine is accumulated in the reaction solution in remarkable amounts In the reaction, ammonia is formed so that the pH of the reaction solution increases as the reaction proceeds Therefore, better results can be obtained by preventing an increase in pH using an acid. The acid that can be used may be any acid unless it seriously inhibits the reaction and examples of the acid include mineral acids such as hydrochloric acid, phosphoric acid, sulfuric acid, nitric acid, etc and organic acids such as formic acid, acetic acid, citric acid, etc.

To collect 2',3'-dideoxyinosine from the reaction solution, there are ordinary purification methods, such as a method utilizing difference in solubility in solvents such as water, etc., a method using ion exchange resin, adsorption resin, etc. Further, quantitative determination of 2',3'-dideoxyinosine was performed by high performance liquid chromatography in a conventional manner Hereafter the present invention will be described in more detail by referring to the following examples.

EXAMPLES

Example 1

To 10 ml of 1M Tris-HCl buffer (pH 7.5) containing 5 g/dl of 2',3'-dideoxyadenosine or adenosine were added 8 units of adenosine deaminase (Type X, derived from bovine spleen) manufactured by Sigma Co., Ltd., 50 mg of DEAMIZYME ® (derived from mold) manufactured by Amano Pharmaceutical Co., Ltd. and 200 mg of washed cells of microorganism shown in Table 1 (culture conditions of the microorganism were the same as in Example 2 described below), respectively, followed by reacting at 30° C. for an hour.

The amount of 2',3'-dideoxyinosine or inosine produced was determined by high performance liquid chromatography. Relative values thereof are shown in Table 1.

In the case of using commercially available microorganism-derived DEAMIZYME ®° manufactured by Amano Pharmaceutical Co., Ltd. and using 2',3'-dideoxyadenosine as substrate, there was little reactivity as compared to the case using adenosine as substrate. To the contrary, in the case of using the microorganism of the present invention, the reactivity was higher in the case of using 2',3'-dideoxyadenosine than in the case of using adenosine as substrate, analogous to the animal-derived enzyme manufactured by Sigma Co., Ltd.

Further, in the case of *Sarcina albida* FERM-P 7048, enzymes that catalyzed the conversion of 2',3'-dideoxyadenosine into 2',3'-dideoxyinosine were partially purified using DEAE-Toyopearl to examine their properties. As a result, it was found that both an enzyme capable of converting adenosine into inosine but not acting on 2',3'-dideoxyadenosine, and an enzyme capable of converting 2',3'-dideoxyadenosine into 2',3'-dideoxyinosine and also converting adenosine into inosine were revealed.

TABLE 1

| Substrate<br>Product | 2',3'-Dideoxyadenosine<br>2',3'-Dideoxyinosine | Adenosine<br>Inosine |
|---|---|---|
| Source of Enzyme | | |
| Adenosine deaminase manufactured by Sigma Co., Ltd. (animal-derived) | 273 | 100 |
| DEAMIZYME ® manufactured by Amano Pharmaceutical Co., Ltd. (microorganism-derived) | 1.4 | 100 |
| Achromobacter candidans FERM-P 8778 | 114 | 100 |
| Brevibacterium pusillum ATCC-19096 | 441 | 100 |
| Escherichia coli FERM-P 7404 | 427 | 100 |
| Proteus rettgeri FERM-P 8196 | 110 | 100 |
| Corynebacterium aquaticum ATCC-14665 | 738 | 100 |
| Sarcina albida FERM-P 7048 | 455 | 100 |

Note: Relative values are shown when the activity of each enzyme or microorganism capable of converting adenosine into inosine.

Example 2

In a 500 ml flask with a shoulder was separately charged 50 ml of medium (pH 7.0) containing 0.5 g/dl of yeast extract, 1.0 g/dl of peptone, 1.0 g/dl of meat extract and 0.5 g/dl of NaCl followed by sterilization. One platinum loop of each microorganism shown in Table 2 which had been preincubated in bouillon agar medium at 30° C. for 16 hours was inoculated on the medium followed by shake culture at 30° C. for 16 hours. After the cells were isolated from the obtained culture solution by centrifugal separation, the cells were washed with 0.05M Tris-HCl buffer (pH 7.2) and further centrifuged to give washed cells.

The washed cells described above were added to 0.05M Tris-HCl buffer (pH 7.2) containing 1 g/dl of 2',3'-dideoxyadenosine in a concentration of 5 g/dl followed by reacting at 30° C. for 2 hours. The amount of 2',3'-dideoxyinosine produced at this stage is shown in Table 2.

TABLE 2

| Strain | 2',3'-Dideoxyinosine Produced (mg/dl) |
|---|---|
| Achromobacter candidans FERM-P 8778 | 785 |
| Acinetobacter lwoffii ATCC-9036 | 52 |
| Aeromonas salmonicida ATCC-14174 | 412 |
| Agrobacterium tumefaciens FERM-P 2343 | 106 |
| Alcaligenes faecalis FERM-P 8030 | 36 |
| Arthrobacter citreus ATCC-11624 | 603 |
| Bacillus firmus ATCC-8247 | 317 |
| Brevibacterium pusillum ATCC-19096 | 931 |
| Cellulomonas flavigena ATCC-491 | 135 |
| Citrobacter freundii ATCC-8090 | 848 |
| Corynebacterium aquaticum ATCC-14665 | 742 |
| Escherichia coli FERM-P 7404 | 816 |
| Enterobacter cloacae ATCC-13047 | 198 |
| Erwinia carotovora FERM-P 2766 | 495 |
| Flavobacterium aquatile ATCC-8375 | 603 |
| Hafnia alvei ATCC-9760 | 416 |
| Klebsiella pneumoniae ATCC-8308 | 186 |
| Kluyvera citrophila FERM-P 8193 | 223 |
| Microbacterium imperiable ATCC-8365 | 109 |
| Micrococcus luteus ATCC-400 | 795 |
| Mycoplana dimorpha ATCC-4279 | 86 |
| Nocardia restricta ATCC-14887 | 107 |
| Planococcus citreus ATCC-15234 | 39 |
| Protaminobacter alboflavus ATCC-8458 | 26 |
| Proteus rettgeri FERM-P 8196 | 896 |
| Pseudomonas oleovorans ATCC-8062 | 113 |
| Rhizobium meliloti FERM-P 8197 | 98 |
| Rhodococcus rhodochrous ATCC-12974 | 109 |
| Salmonella typhimurim FERM-P 9470 | 416 |
| Sarcina albida FERM-P 7048 | 727 |
| Serratia grimesii ATCC-14460 | 213 |
| Staphylococcus epidermidis ATCC-155 | 98 |
| Streptomyces flavovirens IFO-3197 | 145 |
| Vibrio metschnikovii ATCC-7708 | 46 |
| Xanthomonas citri FERM-P 3396 | 465 |

The method of the present invention provides a hitherto unknown method which can produce 2',3'-dideoxyinosine from 2',3'-dideoxyadenosine in a short period of time, by contacting microorganisms supplied at low cost, products containing the same or treated products thereof, with a substrate.

What is claimed as new and desired to be secured by letters patent of the United States is:

1. A method of producing 2',3'-dideoxyinosine, which comprises contacting 2',3'-dideoxyinosine with a culture solution containing a whole microorganism or a fraction thereof wherein said microorganism is selected from the group consisting of *Acinetobacter lwoffii* ATCC-9036, *Aeromonas salmonicida* ATCC-14174, *Alcaligenes faecalis* FERM BP-940, *Arthrobacter citreus* ATCC-11624, *Bacillus firmus* ATCC-8247, *Brevibacterium pusillum* ATCC-19096, *Cellulomonas flavigena* ATCC-491, *Citrobacter freundii* ATCC-8090, *Cornyebacterium aquaticum* ATCC-14665, *Enterobacter cloacae* ATCC-13047, *Flavobacterium aquatile* ATCC-8375, *Hafnia alvei* ATCC-97860, *Klebsiella pneumoniae* ATCC-8308, *Microbacterium imperiable* ATCC-8365, *Micrococcus luteus* ATCC-400, *Mycoplana dimorpha* ATCC-4279, *Nocardia restricta* ATCC-14887, *Planococcus citreus* ATCC-15234, *Protaminobacter alboflavus* ATCC-8458, *Proteus rettgeri* FERM BP-941, *Pseudomonas oleovorans* ATCC08062, Rhodococcus rhodochrous ATCC-12974, Sarcina albida FERM BP-2472, *Arthrobacter ureafaciens* FERM BP-2472, *Serratia grimesii* ATCC-14460, *Staphylococcus epidermidis* ATCC-155, *Streptomyces flavovirens* IFO-3197, *Vibrio metschnikovii* ATCC-7708, and allowing 2',3'-dideoxyinosine to accumulate.

2. The method of claim 1, wherein said microorganisms is *Corynebacterium aquaticum* ATCC-14665 or *Sarcina albida* FERM BP-2472, *Arthrobacter ureafaciens* FERM BP-2472.

3. The method according to claim 1, wherein said culturing is performed under aerobic conditions while controlling the pH of said culture solution to 5 to 8, and at a temperature in the range of 25° to 40° C.

4. The method according to claim 1, wherein said contacting is carried out over a period of from 10 minutes to 10 days.

5. The method according to claim 1, wherein the concentration of 2',3'-dideoxyadenosine is about 1 to 5000 mM.

6. The method according to claim 1, wherein said 2',3'-dideoxyinosine is collected from said culture solution.

* * * * *

UNITED STATES PATENT AND TRADEMARK OFFICE
CERTIFICATE OF CORRECTION

PATENT NO. : 4,970,148

DATED : NOVEMBER 13, 1990

INVENTOR(S) : Kenzo YOKOZEKI et al

It is certified that error appears in the above-identified patent and that said Letters Patent is hereby corrected as shown below:

Column 1, line 22, "unstability" should read --instability--;

Column 2, lines 19-29, "Achromobacter, Acinetobacter, Aeromonas, Agrobacterium, Alcaligenes, Arthrobacter, Bacillus, Brevibacterium, Cellulomonas, Citrobacter, Corynebacterium, Escherichia, Enterobacter, Erwinia, Flavobacterium, Hafnia, Klebsiella, Kluyvera, Microbacterium, Micrococcus, Mycoplana, Nocardia, Planococcus, Protaminobacter, Proteus, Pseudomonas, Rhizobium, Rhodococcus, Salmonella, Sarcina, Serratia, Staphylococcus, Streptomyces, Vibrio or Xanthomonas" should read --*Achromobacter, Acinetobacter, Aeromonas, Agrobacterium, Alcaligenes, Arthrobacter, Bacillus, Brevibacterium, Cellulomonas, Citrobacter, Corynebacterium, Escherichia, Enterobacter, Erwinia, Flavobacterium, Hafnia, Klebsiella, Kluyvera, Microbacterium, Micrococcus, Mycoplana, Nocardia, Planococcus, Protaminobacter, Proteus, Pseudomonas, Rhizobium, Rhodococcus, Salmonella, Sarcina, Serratia, Staphylococcus, Streptomyces, Vibrio or Xanthomonas*--;

line 39, "Examples" should begin a new paragraph.

Column 4, line 53, "manner Hereafter" should read --manner. Hereafter--.

Column 5, line 45, "FERM-P 7048" should read --FERM BP-2472--.

UNITED STATES PATENT AND TRADEMARK OFFICE
CERTIFICATE OF CORRECTION

PATENT NO. : 4,970,148

DATED : NOVEMBER 13, 1990

INVENTOR(S) : Kenzo YOKOZEKI et al

It is certified that error appears in the above-identified patent and that said Letters Patent is hereby corrected as shown below:

Column 6, line 45, "contacting 2',3'-dideoxyinosine" should read --contacting 2',3'-dideoxyadenosine--;

lines 53-54, "*Cornyebacterium*" should read --*Corynebacterium*--;

line 56, "ATCC-97860" should read --ATCC-9760--;

line 62, "ATCC08062" should read --ATCC-8062--.

Signed and Sealed this

Twenty-third Day of February, 1993

*Attest:*

STEPHEN G. KUNIN

*Attesting Officer*    Acting Commissioner of Patents and Trademarks